United States Patent [19]

Miller

[11] 4,389,409
[45] Jun. 21, 1983

[54] 1-(α-N-BUTYLTHIO-2,4-DICHLOROPHENE-THYL)IMIDAZOL-3-yl AND FUNGICIDAL USE THEREOF

[75] Inventor: George A. Miller, Maple Glen, Pa.

[73] Assignee: Rohm and Haas Company, Philadelphia, Pa.

[21] Appl. No.: 779,211

[22] Filed: Mar. 18, 1977

[51] Int. Cl.³ .................... C07D 233/64; A01N 43/50
[52] U.S. Cl. ................................ 424/273 R; 542/413; 542/426; 542/427; 548/341
[58] Field of Search .................... 548/341; 424/273 R; 542/413, 426, 427

[56] References Cited

U.S. PATENT DOCUMENTS 4,055,652 10/1977 Walker ............................. 548/341 X
4,085,209 4/1978 Miller et al. ................. 424/273 R X

FOREIGN PATENT DOCUMENTS 2541333 4/1976 Fed. Rep. of Germany .

*Primary Examiner*—Richard Raymond
*Attorney, Agent, or Firm*—Polly E. Ramstad

[57] ABSTRACT

This invention relates to thiophenethyl imidazoles and triazoles and their acid addition salts. This invention also relates to their preparation and their use as broad spectrum phytopathogenic fungicides.

3 Claims, No Drawings

1-(α-n-BUTYLTHIO-2,4-DICHLOROPHENETHYL)IMIDAZOL-3-yl AND FUNGICIDAL USE THEREOF

SUMMARY OF THE INVENTION

This invention relates to broad spectrum phytopathogenic fungicides of the formula

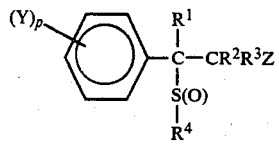

wherein $R^1$, $R^2$ and $R^3$ are independently hydrogen or ($C_1$–$C_8$) alkyl;

$R^4$ is ($C_1$–$C_8$) alkyl, ($C_2$–$C_8$) alkenyl, ($C_2$–$C_8$) aralkyl, ($C_8$–$C_9$) aralkenyl or ($C_6$–$C_{10}$) aryl;

Y is hydrogen, halogen ($C_1$–$C_4$) alkyl, ($C_1$–$C_4$) alkoxy, trihalomethyl, nitro, cyano, thiocyanato, or the group

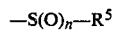

wherein $R^5$ is ($C_1$–$C_4$) alkyl, ($C_3$–$C_8$) cycloalkyl, ($C_7$–$C_9$) aralkyl or ($C_6$–$C_{10}$) aryl;

Z is 1-imidazoyl, 1-(1,2,4-triazolyl) or 4-(1,2,4-triazolyl);

m, n and p are 0, or the integers 1 or 2; and the agronomically acceptable acid addition salts, racemic mixtures and enantiomorphs thereof. A preferred embodiment of this invention is the compounds according to Formula (I) wherein $R^1$, $R^2$ and $R^3$ are independently hydrogen or ($C_1$–$C_4$) alkyl; $R^4$ is ($C_1$–$C_4$) alkyl or ($C_2$–$C_4$) alkenyl; Y is hydrogen or halogen; Z is i-imidazolyl; m is zero; and p is 0 or the integers 1 or 2.

A more preferred embodiment of this invention is the compounds according to Formula (I) wherein $R^1$ and $R^2$ and $R^3$ are hydrogen; $R^4$ is n-butyl or allyl Y is hydrogen or chlorine; Z is 1-imidazolyl; m is zero; and p is the integer 2.

The terms "alkyl", "alkenyl" and "alkynyl" as used in the definition of the terms $R^1$, $R^2$, $R^3$, $R^4$, $R^5$ and Y in the specification and claims is meant to include both branched and straight chained groups of up to eight carbon atoms unless specified otherwise. Typical groups included in these terms are methyl, ethyl, propyl, isopropyl, n-butyl, sec-butyl, t-butyl, pentyl, hexyl, heptyl, octyl; vinyl, allyl, 4-butenyl, 3-pentenyl, 4-hexenyl, 3-heptenyl, 4-octenyl; and propargyl, 4-butynyl, 3-pentynyl, 4-hexynyl, 3-heptynyl, and 4-octynyl respectively.

The terms "aralkyl", "aralkenyl" and "aryl" as used in the definition of $R^4$ and $R^5$ in the specification and claims is meant to include phenyl, naphthyl, benzyl, phenethyl, phenylpropyl, styryl and phenylpropylene groups, the aromatic portion of which can be optionally substituted with up to three substituents preferably with up to two substituents selected from the group consisting of halogen, ($C_1$–$C_4$) alkyl, ($C_1$–$C_4$) alkoxy, trihalomethyl, nitro and cyano.

The compounds of the present invention can be prepared by the following general synthetic route. An appropriately substituted acetophenone of the formula

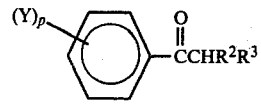

wherein Y, p, $R^2$ and $R^3$ are defined in Formula (I) is reacted either neat or in an appropriate anhydrous solvent such as benzene, toluene, xylene, diethylether, tetrahydrofuran and the like at temperatures from about −20° C. to about 100° C. with a molar or excess amount of a halogenating agent such as bromine, N-bromosuccinimide, chlorine, N-chlorosuccinimide and the like to give the haloacetophenone of Formula III.

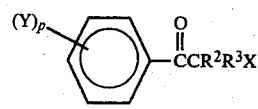

This haloacetophenone is then reacted either neat or in an appropriate solvent such as diethyl ether, tetrahydrofuran, benzene, toluene, xylene, methanol, ethanol, propanol and the like at temperatures from about 0° C. to about 100° C. with a molar or excess amount of imidazole, 1,2,4-triazole or the sodium salt of 1,2,4-triazole to give the 1-imidazolyl, the 4-(1,2,4-triazolyl) or the 1-(1,2,4-triazolyl) compounds of Formula (IV).

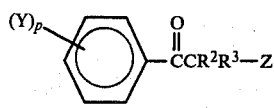

Hydride reduction of the compound of Formula IV with a hydride reducing agent such as sodium borohydride, lithium aluminum hydride, sodium hydride, and the like in an anhydrous solvent such as methanol, diethylether, tetrahydrofuran, dioxane, and the like at temperature from about 0° C. to about 100° C. gives the alcohol of Formula V wherein $R^1$ is hydrogen.

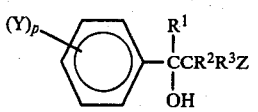

Alternatively, the keto compound of Formula IV can be reacted with a Grignard reagent of the formula R MgX in an anhydrous solvent such as diethyl ether, tetrahydrofuran, dioxane, and the like at temperatures from about 0° C. to about 100° C. to give the alcohol of Formula (VI) wherein R is ($C_1$–$C_8$) alkyl.

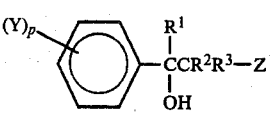

The alcohol of Formula V or VI is then reacted in an appropriate solvent such as benzene, toluene, xylene and the like with a halogenating agent such as thionyl chloride, chlorine, N-chlorosuccinimide and the like at temperatures from about 0° C. to about 120° C. to give the compound of Formula VII.

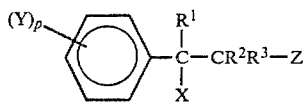

This compound is then reacted in a solvent such as methanol, ethanol, propanal, isopropanol, and the like at temperatures from about 0° C. to about 100° C. with a mercaptan of the formula R⁴SH in the presence of a catalyst such as sodium methoxide, potassium methoxide and the like to give the mercaptan of Formula (VIII)

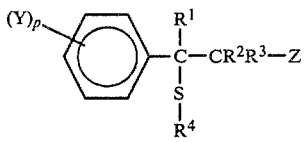

This compound can then be oxidized in an appropriate non-oxidizable solvent such as esters, ketones, aromatic solvents, halogenated hydrocarbons and the like at temperatures from about −5° C. to about 60° C. with one equivalent of an oxidizing agent such as peracetic acid, performic acid, hydrogen peroxide, m-chloroperbenzoic acid, dinitrogen tetroxide, chromium trioxide and the like to give the sulfinyl compound or with at least two equivalents of the above oxidizing agents to give the sulfonyl compound.

The acid addition salts of the compounds of the present invention can be prepared by dissolving the compound in an appropriate solvent or combination of solvents such as methanol, ethanol, acetone, and the like or combinations thereof and treating it with a molar or excess amount of acid. Typical acids which can be utilized to prepare the acid addition salts of the present invention include hydrochloric, hydrobromic, nitric, sulfuric, phosphoric, perchloric, acetic, citric, tartaric, oxalic, malic, maleic, methanesulfonic, p-toluenesulfonic and the like.

Typical compounds encompassed by the present invention include:

1-[2-methylthio-2-(2,4-dichlorophenethyl)]imidazole
1-[2-ethylthio-2-(2,6-dichlorophenethyl)]imidazole
1-[2-propylthio-2-(2,5-dichlorophenethyl)]imidazole
1-[2-n-butylthio-2-(2,4-dibromophenethyl)]imidazole
1-[2-sec-butylthio-2-(2,3-dibromophenethyl)]imidazole
1-[2-t-butylthio-2-(3,5-difluorophenethyl)]imidazole
1-[2-n-pentylthio-2-(3,4-difluorophenethyl)]imidazole
1-[2-n-hexylthio-2-(2,4-diiodophenethyl)]imidazole
1-[2-n-octylthio-2-(4-nitrophenethyl)]imidazole
1-[2-iso-octylthio-2-(2-methylphenethyl)]imidazole
1-[2-vinylthio-2-(3-trifluoromethylphenethyl)-]imidazole
1-[2-allylthio-2-(2,4-diethylphenethyl)]imidazole
1-[2-propargylthio-2-(2,4-dimethoxyphenethyl)-]imidazole
1-[2-cyclohexylthio-2-(2,5-dicyanophenethyl)-]imidazole
1-[2-benzylthio-2-(2,4-dichlorophenethyl)]imidazole
1-[2-phenethylthio-2-(2,4-dibromophenethyl)]imidazole
1-[2-phenylthio-2-(4-thiocyanatophenethyl)]imidazole
1-[2-(2,4-dichlorophenylthio)-2-(2,4-dichlorophenethyl)]imidazole
1-[2-n-butylthio-2-(2,4-dichlorophenethyl)]1,2,4-triazole
4-[2-isopropylthio-2-(2,4-dichlorophenethyl)]1,2,4-triazole
1-[2-allylthio-2-(4-methylsulfonylphenethyl)]1,2,4-triazole
4-[2-propargylthio-2-(4-methylmercaptophenethyl)]1,2,4-triazole
1-[2-sec-butylthio-2-(4-benzylsulfinylphenethyl)]1,2,4-triazole
4-[-2-methyl-2-methylthio-2-(2-trifluoromethylphenethyl)]1,2,4-triazole
1-[2-n-butyl-2-butylthio-2-(4-cyanophenethyl)]1,2,4-triazole
4-[2-neopentyl-2-n-pentylthio-2-(3-nitrophenethyl)]1,2,4-triazole
1-[2-octyl-2-n-octylthio-2-(3,5-dinitrophenethyl)]1,2,4-triazole
1-[2-naphthylthio-2-(2,4-dichlorophenethyl)]imidazole
1-[2-ethyl-2-ethylthio-1,1-dimethyl-2-(2,4-dichlorophenethyl)]imidazole and their agronomically acceptable acid addition salts.

The following examples are provided merely to illustrate the methods of preparation of the compounds of the present invention. These examples are not to be considered in any way as limitations of the scope of this invention.

EXAMPLE 1

A. 1-(2,4-Dichlorophenacyl) imidazole

A 300 ml solution of diethyl ether containing 100 g (0.53 mole) of 2,4-dichloroacetophenone was cooled to 0°-5° C., and treated with 85.0 g (0.53 mole) of bromide and stirred one hour. The organic layer was washed with 3×500 ml portions of saturated sodium bicarbonate solution followed by 3×500 ml portions of water. The aqueous layer was removed and the organic layer treated with a 200 ml portion of methanol containing 108.0 g (1.6 mole) of imidazole and stirred in the cold overnight. The solution was concentrated, poured into 1600 ml of H₂O with separation of an oil, the aqueous layer decanted, and the oil extracted 2×300 ml of methylene chloride. The combined organic phase was washed 2×300 ml of H₂O, dried over magnesium sulfate and concentrated to give 108.8 g (80%) of a red oil. The nitrate salt was formed by treatment of the oil in acetone/ether solution with excess nitric acid, m.p. 161°-163° C. The free base obtained by neutralization was recrystallized from ethanol/water, m.p. 80°-82° C.

B. 1-(α-Hydroxy-2,4-dichlorophenethyl)imidazole

A 150 ml solution of methanol containing 15.6 g (0.061 mole) of 1-(2,4-dichlorophenacyl) imidazole cooled to 0°-5° C. was treated with 1.38 g (0.037 mole) of sodium borohydride in portions. The reaction was stirred ½ hour and the methanol removed at reflux while adding 100 ml of H₂O. The refluxing aqueous mixture was treated with 16 ml of conc. HCl, cooled, and treated with 50 ml of conc. NH₄OH. The mixture was extracted with methylene chloride, dried over MgSO₄, and concentrated to give 11.3 g of a white solid product (66.8%), m.p. 139°-141° C. (from ethanol).

Calc'd for C H Cl N O: C, 51.33 (51.38); H, 3.67 (3.92); Cl, 27.84 (27.57); N. 10.72 (10.89).

C. 1-(α-Chloro-2,4-dichlorophenethyl) imidazole Hydrochloride 1-(α-Hydroxy-2,4-dichlorophenethyl)imidazole, 12.85 g (0.05 mole), was dissolved in 100 ml chloroform and 8.33 g (0.07 mole) thionyl chloride was added to cause immediate formation of a solid precipitate. The mixture was refluxed three hours causing total solution of all solids. No precipitate formed on cooling to ambient temperature. A solid precipitate formed on pouring the chloroform solution into 500 ml of ether. The solid was collected and dried, 8.67 g (55.6%), m.p. 165°–167° C. Both ir and $H^1$ nmr spectra supported the chemical structure. DMSO δ TMS 7.4 (m, 6H, aryl/imidazole); 5.78 (t, 1H, CH); 4.1 (d,2H, $CH_2$).

D. 1-(α-n-Butylthio-2,4-dichlorophenethyl)imidazole

Butyl mercaptan, 4.32 g (0.048 mole), was added to a solution of 2.376 g (0.044 mole) sodium methoxide in 100 ml of methanol and the mixture stirred 30 minutes followed by addition of 10.0 g (0.032 mole) of 1-(α-chloro-2,4-dichlorophenethyl) imidazole hydrochloride in 100 ml methanol. The total mixture was heated to reflux for 4 hours. After cooling, the mixture was poured into an excess of $H_2O$ and the organic layer extracted with ether. The combined ether extracts were washed with 10% NaOH, with $H_2O$, then dried over $MgSO_4$, and filtered. Dry HCl gas was passed through the ether solution to give an oily liquid. Trituration of the oily salt in ethyl acetate was not successful in giving a solid product. The oily salt was dissolved in methanol, treated with excess $NH_4OH$, and converted back to the free base. A total of 4.35 g (42.3%) of the free base was recovered. $H^1$nmr: DMSO δ TMS 7.38 (m, 6H, aryl/imidazole; 4.6 (m, 3H, $CH/CH_2$), 0.6 to 2.76 (m, 9H, $C_4H_9$).

EXAMPLE 2

1-(α-Allylthio-2,4-dichlorophenethyl) imidazole

To a solution of 1.08 g (0.02 mole) of sodium methoxide in 50 ml of methanol was added 1.48 g (0.02 mole) of allyl mercaptan. To this solution was added a solution of 3.12 g (0.01 mole) of 1-(α-chloro-2,4-dichlorophenethyl) imidazole hydrochloride as prepared in Examples 1A to 1C, in 50 ml of methanol. The mixture was heated at reflux for 5 hours, cooled, and poured into 400 ml of $H_2O$. The organic phase was extracted with ether, the combined ether extracts washed with $H_2O$, and dried over $MgSO_4$. Evaporation gave a dark brown oil. The oil was dissolved in a minimum of acetone and treated with an excess of HCl in isopropyl alcohol. Addition of ether caused a gummy solid to separate. Trituration of the gum with ether converted it to a solid that was recrystallized from ethanol-ether with a charcoal treatment. The product, 0.6 g (19%), was a white crystalline solid, m.p. 97°–102° C.

The thiophenethylimidazoles, triazoles and acid addition salts of the present invention can be utilized as broad spectrum phytopathogenic fungicides. These compounds are particularly useful at application rates of 300 ppm in controlling broad bean chocolate spot (*Botrytis cinerea*) on broad bean plants (*Vicia faba*); bean powdery mildew (*Erysiphe polygoni*) on bean plants (var. Dwarf Hort); rice blast (*Piricularia oryzae*) on rice plants (var. Nova 66); tomato late blight (*Phytophthora infestans*) on tomato seedlings (var. Rutgers); barley net blotch (*Helminthosporium teres*) on barley plants (var. Wong); and wheat leaf rust (*Puccinia recondita*) on wheat seedlings (var. Improved Triumph).

The following procedures were employed in evaluating the fungicidal activity of the compounds of this invention.

Broad Bean Chocolate Spot (*Botrytis cinerea*)

Broad bean (*Vicia faba*) seedlings are trimmed to a height of approximately 4–5 inches, 24 hours prior to chemical application. This procedure provides plants of a uniform height and permits rapid and uniform inoculation of the treated plants. *Botrytis cinerea* is cultured on oatmeal agar (OA) slants for 21 days at ambient temperature and low light intensity. Spores are harvested by adding deionized water to the OA slants and scraping the agar surface with a rubber policeman or similar blunt object. The spore suspension is filtered through cheesecloth to remove mycelial and agar fragments and then adjusted to a concentration of 170–200,000 spores per ml with an inoculation medium. The inoculation medium (20 gm glucose, 1 gm ammonium phosphate, 2 gm potassium nitrate, 10 mgm ascorbic acid, 1500 ml deionized water and 500 ml apple juice) is to provide improved spore germination on the surface of the broad bean leaves and stems. Broad bean plants are inoculated by spraying the foliage with the herbicide belt sprayer. Inoculated plants are incubated in a humid environment at 75°–85° F. for 66 hours. Treatment comparisons are made 66–68 hours after inoculation. Typical broad bean chocolate spot symptoms appear as regular circular to lanceolate lesions on plant leaves and stems.

Bean Powdery Mildew (*Erysiphe polygoni*)

Bean plants (var. Dwarf Hort) are thinned to two plants per pot 24 hours prior to chemical application. *Erysiphe polygoni* is cultured on bean leaves for 10–21 days under existing greenhouse conditions. Spores are harvested by adding deionized water containing 0.05 ml of Tween 80 surfactant per 500 ml water to a quart jar containing excised mildew infected bean leaves. The spores are loosened from the leaf surface by shaking the jar. The resulting suspension is filtered through cheesecloth to remove plant debris and adjusted to $2$–$2.5 \times 10^4$ spores per ml. Bean plants are inoculated by spraying the leaves and stems with inoculum until a uniform film of inoculum is observed on the plant. Inoculated plants are maintained under existing greenhouse conditions. Treatment comparisons are made 8–10 days after inoculation. Typical bean powdery mildew signs are circular white mycelial mats (fructications) on the leaf surface.

Rice Blast (*Piricularia oryzae*)

Rice plants (var. Nova 66) are trimmed to a height of approximately 5 inches, 24 hours prior to chemical application. This procedure provides plants of uniform height and permits rapid inoculation of treated plants. *Piricularia oryzae* is cultured on wheat dextrose agar (WDA) plates for 14 days at ambient temperature and normal room light intensity. Spores are harvested by adding deionized water containing 2 gm gelatin and 0.5 gm sodium oleate, per liter, to the WDA plates and scraping the agar surface with a rubber policeman or other similar blunt object. The spore suspension is filtered through cheesecloth to remove mycelial and agar fragments and then adjusted to a concentration of $7.5$–$10 \times 10^4$ spores/ml. Rice plants are inoculated by spraying the leaves and stems with an air brush, using 10 psi air pressure, until a uniform film of inoculum is observed on the leaves. The inoculated plants are incubated in a humid environment (75°–85° F.) for 24 hours prior to being placed into a greenhouse environment. Treatment comparisons are made 7–8 days after inoculation. Initial rice blast lesions appear as small brown necrotic spots on the foliage. The typical lesion is elliptical, 1–2 cm long with a large necrotic gray center and brown margins.

Tomato Late Blight (*Phytophthora infestans*)

Tomato (var. Rutgers) seedlings, 2½–3 inches tall, are fertilized with a water soluble fertilizer 4–5 days prior to chemical application to promote rapid succulent growth and better symptom expression. The pathogen is grown on lima bean agar for 12–15 days at 60° F. and the fungal growth is removed by the agitation of a rubber policeman on a glass rod over the surface of the agar in the presence of deionized water. The inoculum is strained through cheesecloth to remove mycelial and agar fragments and the spore concentration adjusted to 50–60,000 spores/ml. The spore suspension is applied with a DeVilbiss atomizer at 8–10 psi air pressure onto the leaf undersurface until fine droplets are formed. Inoculated seedlings are placed in a humid environment at 60°–62° F. for 40–45 hours, prior to being placed in the greenhouse at 70°–75° F. Treatment comparisons are made 5–6 days after inoculation. Initially, typical tomato late blight symptoms appear as irregular, greenish black, water-soaked patches which enlarge and become brown, with a firm corrugated surface.

Barley Net Blotch (*Helminthosporium teres*)

Barley plants (var. Wong) are trimmed to a height of approximately 2½ inches, 24 hours prior to chemical application. This procedure provides plants of a uniform height and permits rapid inoculation of treated plants. *Helminthosporium teres* is cultured on potato-dextrose agar (PDA) slants for 14 days at ambient temperature and low light intensity. Spores are harvested by adding deionized water to the PDA slants and scraping the agar surface with a rubber policeman or similar blunt object. The spore suspension is filtered through cheesecloth to remove mycelial and agar fragments and then adjusted to a concentration of 15–20,000 spores per ml. One drop of Tween 80 surfactant is added to 100 cc inoculum to provide a more even spore distribution on the surface of the barley leaves. The barley plants are inoculated by spraying the foliage of the plants with a hand sprayer until small droplets of the inoculum are observed on the leaves. Inoculated plants are incubated in a humid environment at 75°–80° F. for 24 hours prior to being placed into the greenhouse under existing conditions. Treatment comparisons are made 6–7 days after inoculation. Typical barley net blotch symptoms initially appear as irregular sunken water-soaked areas which become necrotic as the lesions enlarge.

Wheat Leaf Rust (*Puccinia recondita*)

Wheat plants (var. Pennoll) are trimmed to approximately 2½ inches prior to chemical application to afford a uniform height and ease of inoculation.

Inoculation procedures consist of removal of spores from wheat plants previously infected with leaf rust. Excised plant leaves are placed in a glass jar and deionized water containing 1 drop of B-1956 spreader, sticker is added. The leaf debris is removed by straining the solution through cheesecloth, and the spore concentration is adjusted to give approximately 60,000 spores/ml.

The spore suspension is applied with a "son-of-a-gun" hand sprayer to the surface of the leaves until fine droplets are formed. Inoculated plants are placed in a humid environment at 70°–75° F. for 24 hours prior to being placed in the greenhouse at 70°–75° F. Treatment comparisons are made 6–8 days after inoculation. Typical wheat leaf rust symptoms appear as rust colored pustules on the surface of the leaves.

These thiophenethylimidazoles and triazoles and the acid addition salts thereof are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc. publication "Detergents and Emulsifiers Annual."

In general, the compounds of this invention can be dissolved in certain solvents such as acetone, methanol, ethanol, dimethylformamide, pyridine or dimethyl sulfoxide and such solutions extended with water. The concentrations of the solution can vary from 1% to 90% with a preferred range being 5 to 50%.

For the preparation of emulsifiable concentrates, the compound can be dissolved in suitable organic solvents, or a mixture of solvents, togethers with an emulsifying agent which permits dispersion of the fungicide in water. The concentration of the active ingredient in emulsifiable concentrates is usually 10% to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of 1-(α-allylthio-2,4-dichlorophenethyl)imidazole or triazole, 45 parts of a synthetic precipitated hydrated silicon dioxide sold under the trademark Hi-Sil ® and 5 parts of sodium lignosulfonate (Marasperse ® N-22). In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ® 7.

Dusts are prepared by mixing the 1-(α-allylthio-2,4-dichlorophenethyl) imidazole or triazole with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing 20% to 80% of the active ingredient are commonly made and are subsequently diluted to 1% to 10% use concentration.

These thiophenethylimidazoles and triazoles can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually about 0.1 lb. to 50 lbs. per acre of the active ingredient.

As a seed protectant, the amount of toxicant coated on the seed is usually at a dosage rate of about 0.1 to 20 ounces per hundred pounds of seed. As a soil fungicide the chemical can be incorporated in the soil or applied to the surface usually at a rate of 0.1 to 50 lbs. per acre. As a foliar fungicide, the toxicant is usually applied to growing plants at a rate of 0.25 to 10 lbs. per acre.

Fungicides which can be combined with the fungicides of this invention includes:

(a) dithiocarbamates and derivatives such as:
ferric dimethyldithiocarbamate (ferbam), zinc dimethyldithiocarbamate (Ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as:
dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as:
N-trichloromethylthiotetrahydrophthalimide (captan), N-trichloromethylthiophthalimide (folpet), 2-heptadecyl-2-imidazole acetate (glyodine), 2-octylisothiazolone-3,2,4-dichloro-6-(o-chloroanilino)-s-triazine, diethyl phthalimidophosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-b]quinoxaline (thioquinox), methyl 1-(butylcarbamoyl)-2-benzimidazole carbamate (benomyl), 2-(4'-thiazolyl) benzimidazole (thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, α-(phenyl)-α-(2,4-dichlorophenyl)-5-pyrimidinyl-methanol (triarimol), cis-N-[(1,1,2,2-tetrachloroethyl)thio]-4-cyclohexene-1,2-dicarboximide, 3-[2-(3,5-dimethyl-2-oxycyclohexyl-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclododecyl-2,6-dimethylmorpholine (dodemorph), and 6-methyl-2-oxo-1,3-dithiolo[4,5-b]-quinoxaline (quinomethionate).

(d) miscellaneous halogenated fungicides such as:
tetrachloro-p-benzoquinone (chloranil), 2,3-dichloro-1,4-naphthoquinone (dichlone), 1,4-dichloro-2,5-dimethoxybenzene (chloroneb), 3,5,6-trichloro-o-anisic acid (tricamba), 2,4,5,6-tetrachloroisophthalonitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as:
griseofulvin, kasugamycin and streptomycin;

(f) copper-based fungicides such as:
cuprous oxide, basic cupric chloride, basic copper carbonate, copper naphthenate, and Bordeaux mixture; and (g) miscellaneous fungicides such as:
diphenyl, dodecylguanidine acetate (dodine), phenylmercuric acetate, N-ethylmercuri-1,2,3,6-tetrahydro-3,6-endomethano-3,4,5,6,7,7,-hexachlorophthalimide, phenylmercuric monoethanol ammonium lactate, p-dimethylaminobenzenediazo sodium sulfonate, methyl isothiocyanate, 1-thiocyano-2,4-dinitrobenzene, 1-phenylthiosemicarbazide, nickel-containing compounds calcium cyanamide, lime sulfur, sulfur, and 1,2-bis(3-methoxycarbonyl-2-thioureido)benzene (thiophanate-methyl).

The thiophenethylimidazoles, triazoles and acid addition salts of this invention can be advantageously employed in various ways. Since these imidazoles and triazoles possess broad-spectrum fungicidal activity, they can be employed in the storage of cereal grain. These complexes can also be employed as fungicides in turf, fruit orchard, golf courses and vegetable applications. Other applications of the thiophenethylimidazoles and triazoles of this invention will suggest themselves to those skilled in the art of agriculture and horticulture.

I claim:

1. 1-(alpha-n-butylthio-2,4-dichlorophenethyl)imidazol-3-yl.

2. A fungicidal composition wherein the active ingredient is 1-(α-n-butylthio-2,4-dichlorophenethyl) imidazole.

3. A method for controlling phytopathogenic fungi which comprises applying to the plant, to the plant seed or to the plant habitat, a fungicidally effective amount of a compound according to claim 1.

* * * * *

Disclaimer 4,389,409.—*George A. Miller*, Maple Glen, Pa. 1-(α-n-BUTYLTHIO-2,4-DICHLOROPHENETHYL)IMIDAZOL-3-YL AND FUNGICIDAL USE THEREOF. Patent dated June 21, 1983. Disclaimer filed Apr. 25, 1984, by the assignee, *Rohm and Haas Co.*

Hereby enters this disclaimer to claims 1, 2 and 3 of said patent.

[*Official Gazette June 12, 1984.*]